(12) United States Patent
Kharrat et al.

(10) Patent No.: US 7,319,089 B2
(45) Date of Patent: Jan. 15, 2008

(54) MAUROCALCINE, ANALOGUES THEREOF AND THEIR THERAPEUTICAL USES

(75) Inventors: Riad Kharrat, El Manar I (TN); Kamel Mabrouk, Les Pennes-Mirabeau (TN); Mohammed El-Ayeb, El Ouardia (TN); Hervé Rochat, Mimet (FR); Jean-Marc Sabatier, Chateauneuf-le-Rouge (FR)

(73) Assignee: Cellpep Pharma Inc., Verdun, Quebec (CA)

( * ) Notice: Subject to any disclaimer, the term of this patent is extended or adjusted under 35 U.S.C. 154(b) by 138 days.

(21) Appl. No.: 10/220,833

(22) PCT Filed: Mar. 5, 2001

(86) PCT No.: PCT/EP01/02582

§ 371 (c)(1),
(2), (4) Date: Nov. 14, 2002

(87) PCT Pub. No.: WO01/64724

PCT Pub. Date: Sep. 7, 2001

(65) Prior Publication Data

US 2003/0158108 A1    Aug. 21, 2003

(30) Foreign Application Priority Data

Mar. 3, 2000    (GB) ................................ 0005124.3

(51) Int. Cl.
*A61K 38/00* (2006.01)
*A01N 37/18* (2006.01)

(52) U.S. Cl. ............................................. 514/12; 514/2
(58) Field of Classification Search .................... None
See application file for complete search history.

(56) References Cited

U.S. PATENT DOCUMENTS 6,162,430 A * 12/2000 Hammock et al. .......... 424/93.2
2002/0037275 A1 * 3/2002 Hammock et al. ......... 424/93.6

OTHER PUBLICATIONS

Elements, Atoms, and Molecules, pp. 1-2, printed Jul. 27, 2005, http://www.nyu.edu/pages/mathmol/textbood/compounds.html.*
Esteve, et al., Critical Amino Acid Residues Dtermne the Binding Affinity and the Ca2+ Release Efficacy of Maurocalcine in Skeletal Muscle Cells, The Journal of Biological Science, Sep. 26, 2003, vol. 278, No. 39, pp. 37822-37831.*
On-line Medical Dictionary, Oct. 9, 1997, printed Jul. 27, 2005, p. 1, http://cancerweb.ncl.ac.uk/cgi.bin/omd?immunosuppressive+drug.*
Lazarovici, et al., Insect Toxic Components from the Venom of a Chactoid Scorpion, Scorpio maurus palmuatus (Scorpionidae), The Journal of Biological Chemistry, Jul. 25, 1982, vol. 257, No. 14, pp. 8397-8404.*
Riccardo Zucchi and Simonetta Ronca-Testoni, The Sarcoplasmic Reticulum Ca2+ Channel/Ryanodine Receptor: Modulation by Endogenous Effectors, Drugs and Disease States, Pharmacological Review, 1997, p. 1-51.*
Dulhunty, et al., Agonists and antagonists of the cardiac ryanodine receptor: Potential therapeuctic agents?, Pharacology & Therapeutics, 2006 (Article in Press), pp. 1-17.*
George, et al., Ryanodine receptor and ventricular arrhythmias: Emerging trends in mutation, mechanisms and therapies, Journal of Molecular and Cellular Cardiology, 2006 (Article In Press), pp. 1-17.*
Rudinger, Peptide Hormones, (Jun. 1976) 1,5-6.*
PubMed, www.pubmed.gov, 2006, pp. 1-42, http://www.ncbi.nih.gov/entrez/quiry.fcgi, printed Dec. 20, 2006.*
El-Hayek, et al., Peptide Probe of Ryanodine Receptor Function, The Journal of Biological Chemistry, Dec. 1, 1995, vol. 270, No. 48, pp. 28696-28704.*
Zamudio Fernando Z et al: "Primary Structure and Synthesis of Imperatoxin", Febs Letters, 1997, pp. 385-389, vol. 405, No. 3.
Zamudio Fernando Z et al:"The Mechanism of Inhibition of Ryanodine Receptor Channels by Imperatoxin", Journal of Biological Chemistry, 1997, pp. 11886-11894, vol. 272, No. 18.
Fajloun Z et al.: "Chemical Synthesis and Characterization of Maurocalcine", Febs Letters, Mar. 10, 2000, pp. 179-185, vol. 469, No. 2-3.
Mosbah Amor et al.: "A New Fold in the Scorpian Toxin Family", Proteins, Aug. 15, 2000, pp. 436-442, vol. 40, No. 3.

* cited by examiner

*Primary Examiner*—Cecilia J. Tsang
*Assistant Examiner*—Jennifer I Harle
(74) *Attorney, Agent, or Firm*—Cherskov & Flaynik

(57) ABSTRACT

Maurocalcine, a novel toxin isolated from the venom of the Tunisian chactidae scorpion *Scorpio maurus palmatus*, has the amino acid sequence GDCLPHLKLCKENKD-CCSKKCKRRGTNIEKRCR (SEQ. ID. No. 1). It potently and reversibly modifies channel gating behaviour of type 1 ryanodine receptor (RyR1) by inducing prominent subconductance behavior. Maurocalcine and its bioactive structural analogues—preferably those containing the KKCKRR motif corresponding to part of the II-III loop of the alpha1S subunit of the voltage-dependent skeletal muscle calcium channel dihydropyridine receptor—appear to possess a therapeutic potential, notably as candidate immuno-suppressive drugs, and for the treatment of pathologies in humans that may involve a dysfunction of calcium channels.

1 Claim, 1 Drawing Sheet

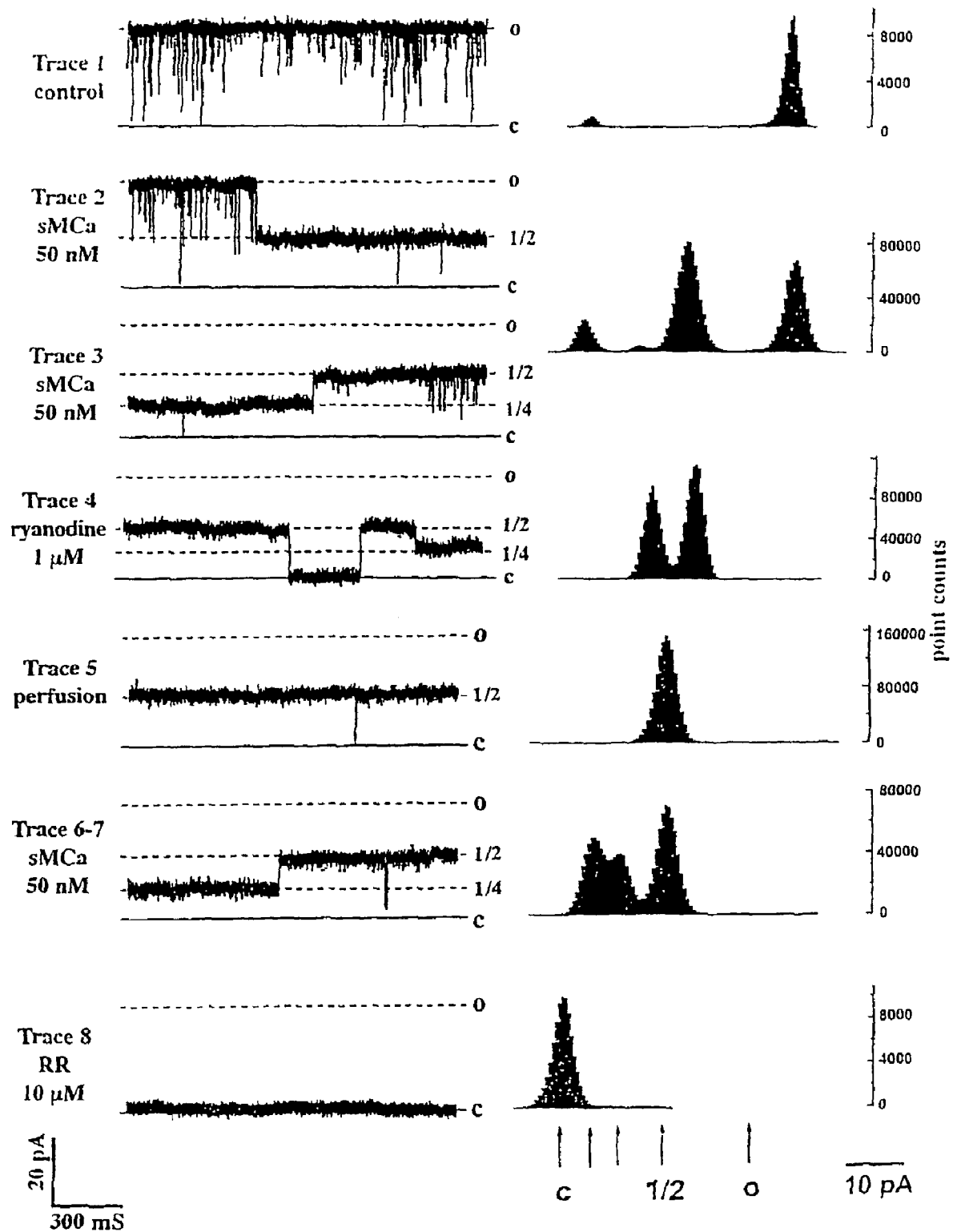

SEQUENCE LISTING

<160> NUMBER OF SEQ ID NOS: 1

<210> SEQ ID NO 1
<211> LENGTH: 33
<212> TYPE: PRT
<213> ORGANISM: Scorpio maurus palmatus

<400> SEQUENCE: 1

```
Gly Asp Cys Leu Pro His Leu Lys Leu Cys Lys Glu Asn Lys Asp Cys
1               5                   10                  15
Cys Ser Lys Lys Cys Lys Arg Arg Gly Thr Asn Ile Glu Lys Arg Cys
            20                  25                  30
Arg
```

MAUROCALCINE, ANALOGUES THEREOF AND THEIR THERAPEUTICAL USES

DESCRIPTION

The invention relates to maurocalcine, its bioactive structural analogues and to their therapeutical uses.

Maurocalcine (MCa) is a novel toxin isolated from the venom of the Tunisian chactidae scorpion *Scorpio maurus palmatus*. It is a 33-mer basic peptide (amino acid sequence: GDCLPHLKLCKENKDCCSKKCKRRGTNIEKRCR, SEQ. ID. No. 1) cross-linked by three disulphide bridges (located between Cys3-Cys17, Cys10-Cys21 and Cys16-Cys32). It shares a high sequence identity with Imperatoxin A (IpTx A), a scorpion toxin from the venom of Pandinus imperator but not with other known scorpion toxins. The MCa and IpTx A, although they are likely to adopt a grossly similar conformation are peculiar in terms of structural properties since they do not possess the consensus motif [S]C[S]CXXXC[S](G/A/S)XC[S]CXC[S] wherein [S] is a segment of variable length and X is an unspecified amino acid (the consensus motif is also known as the alpha/beta scaffold) found in all known scorpion toxins independently of their size, primary structure and pharmacological specificity. This motif is found in either three or four disulphide-bridged scorpion toxins. At, the structural level, this motif consists of an alpha-helix connected to an antiparallel beta-sheet by two disulphide bridges. Instead MCa contains the "inhibitor cystine knot" motif which is found in some spider and marine snail venom toxins. The inhibitor knot motif is $CX_{3-7}CX_{3-6}CX_{0-5}CX_{1-4}CX_{4-13}C$ (where $CX_{3-7}$ indicates a Cys residue followed by from 3 to 7 unspecified amino acid residues selected from the twenty occurring naturally).

We have synthesized maurocalcine by means of an optimised solid-phase method (see Example 1 below), and the synthetic product (sMCa) was characterized.

In vitro, electrophysiological experiments based on recordings of single-channels incorporated into planar lipid bilayers (see Example 2 below) showed that sMCa potently and reversibly modifies channel gating behaviour of type 1 ryanodine receptor (RyR1) by inducing prominent subconductance behavior. Therefore, sMCa and its bioactive structural analogues—preferably those containing the KKCKRR motif corresponding to part of the II-III loop of the alpha1S subunit of the voltage-dependent skeletal muscle calcium channel dihydropyridine receptor—appear to possess a therapeutic potential, notably as candidate immuno-suppressive (cyclosporine-like) drugs, and for the treatment of pathologies in humans that may involve a dysfunction of calcium channels. Such pathologies include malignant hyperthermia (MF) which is a potentially lethal condition that is manifested in humans as an acute increase of body temperature in response to stress and exposure to volatile anaesthetics. Further possible uses arise from alterations in the ryanodine receptor calcium release channel correlating with Alzheimer's disease neurofibrillary and beta-amyloid pathologies, from drugs active on ryanodine receptors such as dandrolene having protective effects in post-ischemic reperfusion myocardial damage, and from the fact that FKBP12-deficient mice (maurocalcine competes with FKBP12 for binding onto the ryanodine receptor) have severe dilated cardiomyopathy and ventricular septal defects that mimic a human congenital heart disorder.

In view of the activity on ryanodine type I receptors (RYR1), other potential uses of sMCa are for inhibition of the proliferation and stimulation of pigmentation of human melanocytes (possible application in melanoma or pigmentation anomalies); modulation of cell apoptosis; and as a heparin antidote. SMCa may also act on Arg-vasopressin activity and as a modulator of GABAergic synapses.

IpTx A was reported to activate $Ca^{2+}$ release channel/ryanodine receptors of mammalian skeletal (RyR1) and cardiac muscles (RyR2). Together with inositol 1,4,5-triphosphate (IP3) receptors, RyR controls the intracellular $Ca^{2+}$ permeability of various cell-types, and is central in the process of excitation-contraction of muscle tissues. Ligands such as toxins that specifically interact with RyR are molecular probes to investigate both the structure of the receptor and its role in excitation-contraction coupling. The sMCa was tested by electrophysiology in vitro for its action on $Ca^{2+}$ flux through RyR1 channels incorporated into planar bilayer lipid membranes. Our data demontrate that sMCa is a new toxin active on RyR1 and that it binds onto a site different from that of ryanodine itself. Briefly, the physiological effect and molecular target of sMCa were investigated.

Intracerebroventricular injections of sMCa produced lethal effects in mice but at high dose only ($LD_{50}$ value of 20 µg per mouse). sMCa had no significant sequence identity with any known scorpion toxin except IpTx A. Since IpTx A targets RyR1 of skeletal muscle, we wanted to determine whether sMCa was active on this receptor. Therefore, we performed electrophysiological experiments on single RyR1 channels incorporated into planar lipid bilayers, and showed that nanomolar concentration of sMCa potently activates RyR1 channels. Indeed, sMCa added to the cytoplasmic compartment (cis side of the skeletal RyR1) induces the appearance of subconductance states corresponding to part of the typical full conductance seen with RyR1. A similar observation as made for the action of IpTx A. The data also suggest that the peptide is able to simultaneously bind to the RyR1 receptor together with ryanodine. This result was not surprising since it was reported that IpTx A is capable of enhancing [3H]-ryanodine binding. Since sMCa induces the appearance of long-lived subconductance, in a similar though not identical manner as IpTx A, it is expected to induce net $Ca^{2+}$ release from the SR. In this regard, sMCa differs from IpTx A in that it stabilizes multiple conductance states whereas the latter seems to favour only the ⅓, conductance state. It has recently been noted that IpTx A shares a structural homology with a segment of the II-III loop of the skeletal muscle dihydropyridine receptor (a1S subunit) that has been proposed to act as an activator of the RyR1. This homology concerns a cluster of basic amino acid residues (KKCKRR motif) at positions 19 to 24. Based on this observation, it appears that IpTx A is a peptide mimetic of the dihydropyridine receptor II-III loop, itself an endogenous effector structure that is crucial for excitation-contraction coupling. Remarkably, this basic motif is entirely conserved in MCa. The similarities in structure and function between IpTX A and MCa suggest that they may share the same binding site onto RyR1 and that this site could overlap a potential excitation-contraction signal transduction locus. The binding site of IpTx A has been located to the cytoplasmic moiety of RyR1 between the clamp and handle domains, away from the transmembrane pore supporting an allosteric mechanism of action of these toxins as opposed to the one involving direct positioning withinthe ion conducting channel.

EXAMPLE 1 sMCa was obtained by the solid-phase method (Merrifield, 1986) using an automated peptide synthesizer (Model 433A, Applied Biosystems Inc.). Peptide chains were assembled stepwise on 0.25 mequiv. of HMP resin (1% cross-linked; 0.89 mequiv. of amino group/g) using 1 mmol of N-α-fluorenylmethyloxycarbonyl (Fmoc) amino acid derivatives. The side chain-protecting groups used for trifunctional residues were: trityl (Trt) for Cys, and Asn; t-butyl (t-Bu) for Ser, Thr, Glu, and Asp; pentamethylchroman (Pmc) for Arg, and t-butoxycarbonyl (Boc) for Lys. N-α-amino groups were deprotected by treatment with 18% and 20% (v/v) piperidine/N-methylpyrrolidone for 3 and 8 min, respectively. The Fmoc-amino acid derivatives were washed several times with N-methylpyrrolidone (5×1 min) and coupled (20 min) as their hydroxybenzotriazole active esters (OBt) in N-methylpyrrolidone (4-fold excess). After peptide chain assembly was completed and the N-terminal Fmoc group removed, the peptide resin (about 1.8 g) was treated under stirring for 3 h at room temperature with a mixture of trifluoroacetic acid/$H_2O$/thioanisole/ethanedithiol (88:5:5:2, v/v), in the presence of crystalline phenol (2.25 g) in a final volume of 30 ml per gram of peptide resin. The peptide mixture were then filtered to remove resin, and the filtrate was precipitated and washed three times by adding cold t-butylmethyl ether. The resulting crude peptide was pelleted by centrifugation (3,000 g; 8 min) and the supernatant was discarded. The peptide was dissolved in $H_2O$ and freeze dried. The reduced peptide was then dissolved in 200 mM Tris/HCl buffer, pH 8.3, at a final concentration of 2.5 mM and stirred under air to allow folding (72 h, room temperature). The target oxidized product, sMCa, was purified to homogeneity first by semi-preparative reversed-phase high-pressure liquid chromatography (HPLC) (Perkin-Elmer, C18 Aquapore ODS 20 mm, 250×10 mm) by means of a 60-min linear gradient of 0.08% (v/v) trifluoroacetic acid (TFA)/0% to 30% acetonitrile in 0.1% (v/v) TFA/$H_2O$ at a flow rate of 6 ml/min ($\lambda$=230 nm). A second step of purification of sMCa was achieved by ion exchange chromatography on a carboxymethyl cellulose matrix using 10 mM (buffer A) and 500 mM (buffer B) sodium phosphate buffers, pH 9 (60-min linear gradient from 0% to 60% buffer B at a flow rate of 1 ml/min). The homogeneity and identity of sMCa was assessed by: (i) analytical C18 reverse-phase HPLC (Merck, C18 Lichrospher 5 mm, 4×200 mm) using a 60-min linear gradient of 0.08% (v/v) TFA/0% to 60% acetonitrile in 0.1% (v/v) TFA/H2O at a flow rate of 1 ml/min; (ii) amino acid analysis after acidolysis (6 N HCl/2% (w/v) phenol, 20 h, 118° C., $N_2$ atmosphere); and (iii) mass determination by matrix-assisted laser desorption ionization-time of flight (MALDI-TOF) mass spectrometry.

EXAMPLE 2

Single-channel recording: $Cs^+$ current through single RyR1 channels incorporated into planar lipid bilayers (BLM) was measured in an asymmetric CsCl (10:1 cis:trans) solution. The BLM was formed from a mixture of phosphatidylethanolamine and phosphatidylcholine (5:2, w/w) at 30-50 mg/ml in decane, across a 150-300 mm aperture in a 1.0 ml polystyrene cup. SR vesicles were added to the cis side of chamber at a final concentration of 0.1-10 mg/ml. The cis solution contained 500 mM CsCl, ~7 mM $CaCl_2$, 20 mM HEPES, pH 7.4, and the trans solution contained 50 mM CsCl, 7 mM free $Ca^{2+}$, 20 mM HEPES, pH 7.4. The monovalent cation $Cs^+$ was used as permeant ion instead of divalent cations (such as $Ca^{2+}$) owing to its better permeability through RyR1. After a single fusion event, sarcoplasmic reticulum (SR) vesicles in cis chamber were quickly removed by perfusion with 9× volume of is solution. Single-channel current was measured under voltage clamp using a Dagan 3900 amplifier (Dagan Instruments, Minneapolis, Minn.). Holding potentials were with respect to the trans (ground) chamber, and positive current was defined as current flowing from cis to trans. Current signals were captured at 10 kHz and filtered at 1 kHz using a four pole Bessel filter. Data was digitized with a Digidata 1200 interface (Axon Instruments, Burlingame, Calif.) and stored on computer for subsequent analysis. Unless otherwise stated, test chemicals were sequentially added to the cis solution after an initial period of recording control channel behaviour. Single channel activity was analyzed with pCLAMP 7.0 (Axon Instruments). Current levels were analyzed by mean-variance analysis and peaks in the all-points amplitude histogram were fitted with Gaussian functions. The all-points amplitude histograms were constructed from selected segments-of data 20-150 sec in length to quantify the incidence of full and subconductance states.

Results: we determined the effect and molecular target of sMCa. sMCa had no significant sequence identity with any known scorpion toxin except IpTx A. Since IpTx A targets RyR1 of skeletal muscle, we wanted to determine whether sMCa was also active on this receptor. To test this hypothesis, we performed electrophysiological experiments on single RyR1 channels incorporated into planar lipid bilayers. The data illustrate that nanomolar concentration of sMCa applied on the cis side (cytoplasmic side) dramatically modified the channel gating behavior of the RyR1. No effect of the toxin was observed on the trans side (luminal side) suggesting a cytoplasmic site of action of the toxin. Of the twelve channels tested, all exhibited similar responses to sMCa (5 nM to 1 µM) added to the cis chamber. The predominant action of sMCa was to rapidly induce long-lived subconductances, mainly having one-half the characteristic full conductance (traces 1-3). To a smaller extent, conductance approximating one-quarter the full conductance level were observed and were evident in the amplitude histograms. Four out of five channels modified by sMCa were shown to be subsequently modified by the alkaloid ryanodine (1 µM) confirming the identity of the channel as RyR1. Five out of six channels modified by sMCa were blocked by 10 mM ruthenium red. With both sMCa and ryanodine present, RyR exhibited very stable and long-lived half and quarter subconductances approximating 50.5% and 29.3% of the characteristic control conductance level (trace 4). Once the channel was modified by sMCa and ryanodine, perfusion of the cis chamber only reversed the sMCa-induced quarter states, whereas the ryanodine-mediated half-states persisted (trace 5) which indicates that ryanodine and sMCa are probably able to bind simultaneously and on separate sites onto the RyR1. Re-introduction of sMCa cis resulted in rapid reappearance of the stable 51% and 29% conductance transitions (trace 6-7). Final addition of ruthenium red completely blocked the ryanodine/sMCa modified channel (trace 8).

The invention claimed is:

1. A Synthetic peptide having the amino acid sequence GDCLPHLKLCKENKDCCSKKCKRRGTNIEKRCR (SEQ. ID. No. 1) also known as Maurocalcine.

* * * * *